(12) United States Patent
Jarral et al.

(10) Patent No.: US 10,806,579 B2
(45) Date of Patent: Oct. 20, 2020

(54) HEART VALVE REPAIR IMPLANT FOR TREATING TRICUSPID REGURGITATION

(71) Applicant: BOSTON SCIENTIFIC SCIMED, INC., Maple Grove, MN (US)

(72) Inventors: Omar Jarral, London (GB); Aiden Flanagan, Kilcolgan (IE); Patricia McAfee, Galway (IE); Tim O'Connor, Galway (IE); Jan Weber, Maastricht (NL)

(73) Assignee: Boston Scientific Scimed, Inc., Maple Grove, MN (US)

( * ) Notice: Subject to any disclaimer, the term of this patent is extended or adjusted under 35 U.S.C. 154(b) by 179 days.

(21) Appl. No.: 16/166,628

(22) Filed: Oct. 22, 2018

(65) Prior Publication Data

US 2019/0117388 A1 Apr. 25, 2019

Related U.S. Application Data

(60) Provisional application No. 62/574,833, filed on Oct. 20, 2017.

(51) Int. Cl.
*A61F 2/24* (2006.01)
*A61B 17/04* (2006.01)
*A61B 17/00* (2006.01)

(52) U.S. Cl.
CPC .......... *A61F 2/246* (2013.01); *A61B 17/0401* (2013.01); *A61F 2/2409* (2013.01);
(Continued)

(58) Field of Classification Search
CPC ...... A61F 2/246; A61F 2/2463; A61F 2/2409; A61F 2/2427; A61F 2/2466; A61B 17/08;
(Continued)

(56) References Cited

U.S. PATENT DOCUMENTS

| 4,423,525 A | 1/1984 | Vallana et al. |
| 4,493,329 A | 1/1985 | Crawford et al. |

(Continued)

FOREIGN PATENT DOCUMENTS

| EP | 1759663 A2 | 3/2007 |
| EP | 1836971 A2 | 9/2007 |

(Continued)

*Primary Examiner* — Brian A Dukert
(74) *Attorney, Agent, or Firm* — Seager, Tufte & Wickhem LLP

(57) ABSTRACT

A heart valve repair implant may include a first implant section having a first axial core, and a plurality of spines extending radially outward from the first axial core in an expanded configuration; a second implant section having a second axial core configured to slide over the first axial core, and a mesh portion configured to extend radially outward from the second axial core in an expanded configuration; a third implant section having a central tensioning element extending through the first axial core, and a plurality of arms extending radially outward from the central tensioning element and configured to extend axially between the plurality of spines and through the mesh portion; and a securement element disposed on the central tensioning element.

20 Claims, 14 Drawing Sheets

(52) U.S. Cl.
CPC .......... *A61F 2/2427* (2013.01); *A61F 2/2463* (2013.01); *A61F 2/2466* (2013.01); *A61B 17/0487* (2013.01); *A61B 2017/00243* (2013.01); *A61B 2017/00783* (2013.01); *A61B 2017/0406* (2013.01); *A61B 2017/0409* (2013.01); *A61B 2017/0417* (2013.01); *A61B 2017/0437* (2013.01); *A61B 2017/0464* (2013.01); *A61B 2017/0496* (2013.01)

(58) Field of Classification Search
CPC .......... A61B 17/10; A61B 2017/00243; A61B 2017/00783
See application file for complete search history.

(56) References Cited

U.S. PATENT DOCUMENTS

| | | | |
|---|---|---|---|
| 4,625,727 A | 12/1986 | Leiboff | |
| 4,778,468 A | 10/1988 | Hunt et al. | |
| 4,853,986 A | 8/1989 | Allen | |
| 5,108,420 A | 4/1992 | Marks | |
| 5,330,521 A | 7/1994 | Cohen | |
| 5,450,860 A | 9/1995 | O'Connor | |
| 5,473,812 A | 12/1995 | Morris et al. | |
| 5,776,178 A | 7/1998 | Pohndorf et al. | |
| 5,792,400 A | 8/1998 | Talja et al. | |
| 5,843,120 A | 12/1998 | Israel et al. | |
| 5,957,953 A | 9/1999 | DiPoto et al. | |
| 6,027,523 A | 2/2000 | Schmieding | |
| 6,298,272 B1 | 10/2001 | Peterfeso et al. | |
| 6,299,635 B1 | 10/2001 | Frantzen | |
| 6,332,893 B1 | 12/2001 | Mortier et al. | |
| 6,575,976 B2 | 6/2003 | Grafton | |
| 6,613,078 B1 | 9/2003 | Barone | |
| 6,613,079 B1 | 9/2003 | Wolinsky et al. | |
| 6,616,684 B1 | 9/2003 | Vidlund et al. | |
| 6,626,899 B2 | 9/2003 | Houser et al. | |
| 6,626,930 B1 | 9/2003 | Allen et al. | |
| 6,629,921 B1 | 10/2003 | Schweich, Jr. et al. | |
| 6,641,597 B2 | 11/2003 | Burkhart et al. | |
| 6,702,846 B2 | 3/2004 | Mikus et al. | |
| 6,723,038 B1 | 4/2004 | Schroeder et al. | |
| 6,730,118 B2 | 5/2004 | Spenser et al. | |
| 6,797,001 B2 | 9/2004 | Mathis et al. | |
| 6,884,250 B2 | 4/2005 | Monassevitch et al. | |
| 6,908,478 B2 | 6/2005 | Alferness et al. | |
| 7,101,395 B2 | 9/2006 | Tremulis et al. | |
| 7,125,421 B2 | 10/2006 | Tremulis et al. | |
| 7,144,363 B2 | 12/2006 | Pai et al. | |
| 7,159,593 B2 | 1/2007 | McCarthy et al. | |
| 7,169,187 B2 | 1/2007 | Datta et al. | |
| 7,175,625 B2 | 2/2007 | Culbert | |
| 7,186,262 B2 | 3/2007 | Saadat | |
| 7,201,772 B2 | 4/2007 | Schwammenthal et al. | |
| 7,311,728 B2 | 12/2007 | Solem et al. | |
| 7,316,706 B2 | 1/2008 | Bloom et al. | |
| 7,316,710 B1 | 1/2008 | Cheng et al. | |
| 7,338,506 B2 | 3/2008 | Caro | |
| 7,351,256 B2 | 4/2008 | Hojeibane et al. | |
| 7,390,329 B2 | 6/2008 | Westra et al. | |
| 7,530,995 B2 | 5/2009 | Quijano et al. | |
| 7,547,321 B2 | 6/2009 | Silvestri et al. | |
| 7,549,983 B2 | 6/2009 | Roue et al. | |
| 7,618,449 B2 | 11/2009 | Tremulis et al. | |
| 7,628,797 B2 | 12/2009 | Tieu et al. | |
| 7,632,303 B1 | 12/2009 | Stalker et al. | |
| 7,666,204 B2 | 2/2010 | Thronton et al. | |
| 7,771,467 B2 | 8/2010 | Svensson | |
| 7,780,726 B2 | 8/2010 | Seguin | |
| 7,803,187 B2 | 9/2010 | Hauser | |
| 7,871,433 B2 | 1/2011 | Lattouf | |
| 7,988,725 B2 | 8/2011 | Gross et al. | |
| 7,991,484 B1 | 8/2011 | Sengupta et al. | |
| 7,993,368 B2 | 8/2011 | Gambale et al. | |
| 8,010,207 B2 | 8/2011 | Smites et al. | |
| 8,029,518 B2 | 10/2011 | Goldfarb et al. | |
| 8,052,592 B2 | 11/2011 | Goldfarb et al. | |
| 8,108,054 B2 | 1/2012 | Helland | |
| 8,142,493 B2 | 3/2012 | Spence et al. | |
| 8,236,013 B2 | 8/2012 | Chu | |
| 8,262,724 B2 | 9/2012 | Seguin et al. | |
| 8,262,725 B2 | 9/2012 | Subramanian | |
| 8,267,981 B2 | 9/2012 | Boock et al. | |
| 8,323,335 B2 | 12/2012 | Rowe et al. | |
| 8,332,051 B2 | 12/2012 | Sommer et al. | |
| 8,470,028 B2 | 6/2013 | Thornton et al. | |
| 8,475,525 B2 | 7/2013 | Maisano et al. | |
| 8,628,571 B1 | 1/2014 | Hacohen et al. | |
| 8,967,594 B2 | 2/2015 | Maisano et al. | |
| 2002/0032481 A1 | 3/2002 | Gabbay | |
| 2002/0151961 A1 | 10/2002 | Lashinski et al. | |
| 2002/0177904 A1 | 11/2002 | Huxel et al. | |
| 2003/0167071 A1 | 9/2003 | Martin et al. | |
| 2003/0229350 A1 | 12/2003 | Kay | |
| 2003/0236568 A1 | 12/2003 | Hojeibane et al. | |
| 2004/0024451 A1 | 2/2004 | Johnson et al. | |
| 2004/0181287 A1 | 9/2004 | Gellman | |
| 2004/0186566 A1 | 9/2004 | Hindrichs et al. | |
| 2004/0193092 A1 | 9/2004 | Deal | |
| 2004/0236419 A1 | 11/2004 | Milo | |
| 2004/0260389 A1 | 12/2004 | Case et al. | |
| 2005/0016560 A1 | 1/2005 | Voughlohn | |
| 2005/0090827 A1 | 4/2005 | Gedebou | |
| 2005/0107812 A1 | 5/2005 | Starksen et al. | |
| 2005/0107871 A1 | 5/2005 | Realyvasquez et al. | |
| 2005/0177228 A1 | 8/2005 | Solem et al. | |
| 2005/0203606 A1 | 9/2005 | VanCamp | |
| 2005/0216039 A1 | 9/2005 | Lederman | |
| 2006/0052821 A1 | 3/2006 | Abbott et al. | |
| 2006/0106423 A1 | 5/2006 | Weisel et al. | |
| 2006/0129166 A1 | 6/2006 | Lavelle | |
| 2006/0161265 A1 | 7/2006 | Levine et al. | |
| 2006/0229708 A1 | 10/2006 | Powell et al. | |
| 2006/0241748 A1 | 10/2006 | Lee et al. | |
| 2006/0282161 A1 | 12/2006 | Huynh et al. | |
| 2007/0016287 A1 | 1/2007 | Cartledge et al. | |
| 2007/0021781 A1 | 1/2007 | Jervis et al. | |
| 2007/0038221 A1 | 2/2007 | Fine et al. | |
| 2007/0049942 A1 | 3/2007 | Hindrichs et al. | |
| 2007/0049970 A1 | 3/2007 | Belef et al. | |
| 2007/0061010 A1 | 3/2007 | Hauser et al. | |
| 2007/0066863 A1 | 3/2007 | Rafiee et al. | |
| 2007/0093869 A1 | 4/2007 | Bloom et al. | |
| 2007/0118151 A1 | 5/2007 | Davidson | |
| 2007/0162107 A1 | 7/2007 | Haug et al. | |
| 2007/0198082 A1 | 8/2007 | Kapadia et al. | |
| 2007/0203391 A1 | 8/2007 | Bloom et al. | |
| 2007/0250160 A1 | 10/2007 | Rafiee | |
| 2007/0276437 A1 | 11/2007 | Call et al. | |
| 2007/0282375 A1 | 12/2007 | Hindrichs et al. | |
| 2008/0003539 A1 | 1/2008 | Lundgren | |
| 2008/0035160 A1 | 2/2008 | Woodson et al. | |
| 2008/0077231 A1 | 3/2008 | Heringes et al. | |
| 2008/0262609 A1 | 10/2008 | Gross et al. | |
| 2008/0275469 A1 | 11/2008 | Fanton et al. | |
| 2008/0288044 A1 | 11/2008 | Osborne | |
| 2008/0288062 A1 | 11/2008 | Andrieu et al. | |
| 2009/0084386 A1 | 4/2009 | McClellan et al. | |
| 2009/0118776 A1 | 5/2009 | Kelsch | |
| 2009/0149872 A1 | 6/2009 | Gross et al. | |
| 2009/0171439 A1 | 7/2009 | Nissl | |
| 2009/0216265 A1 | 8/2009 | DeVries et al. | |
| 2009/0254103 A1 | 10/2009 | Deutsch | |
| 2009/0259307 A1 | 10/2009 | Gross et al. | |
| 2009/0264995 A1 | 10/2009 | Subramanian | |
| 2009/0300629 A1 | 12/2009 | Navon et al. | |
| 2009/0326648 A1 | 12/2009 | Machold et al. | |
| 2010/0121349 A1 | 5/2010 | Meier et al. | |
| 2010/0130992 A1 | 5/2010 | Machold et al. | |
| 2010/0161041 A1 | 6/2010 | Maisano et al. | |
| 2010/0161042 A1 | 6/2010 | Maisano et al. | |
| 2010/0161043 A1 | 6/2010 | Maisano et al. | |
| 2010/0161047 A1 | 6/2010 | Cabiri | |
| 2010/0168791 A1 | 7/2010 | Kassab et al. | |

(56) References Cited

U.S. PATENT DOCUMENTS

| | | |
|---|---|---|
| 2010/0174358 A1 | 7/2010 | Rabkin et al. |
| 2010/0185278 A1 | 7/2010 | Schankereli |
| 2010/0204662 A1 | 8/2010 | Orlov |
| 2010/0211166 A1 | 8/2010 | Miller et al. |
| 2010/0217382 A1 | 8/2010 | Chau et al. |
| 2010/0234935 A1 | 9/2010 | Bashiri et al. |
| 2010/0249908 A1 | 9/2010 | Chau et al. |
| 2010/0280603 A1 | 11/2010 | Maiano et al. |
| 2010/0280604 A1 | 11/2010 | Zipory et al. |
| 2010/0280605 A1 | 11/2010 | Hammer et al. |
| 2010/0286628 A1 | 11/2010 | Gross |
| 2010/0286767 A1 | 11/2010 | Zipory et al. |
| 2010/0324598 A1 | 12/2010 | Anderson |
| 2011/0022164 A1 | 1/2011 | Quinn et al. |
| 2011/0029066 A1 | 2/2011 | Gilad et al. |
| 2011/0035000 A1 | 2/2011 | Nieminen et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0106245 A1 | 5/2011 | Miller et al. |
| 2011/0106247 A1 | 5/2011 | Miller et al. |
| 2011/0112619 A1 | 5/2011 | Foster et al. |
| 2011/0112632 A1 | 5/2011 | Chau et al. |
| 2011/0184510 A1 | 7/2011 | Maisano et al. |
| 2011/0238088 A1 | 9/2011 | Bolduc et al. |
| 2011/0238112 A1 | 9/2011 | Kim et al. |
| 2011/0251678 A1 | 10/2011 | Eidenschink et al. |
| 2011/0264208 A1 | 10/2011 | Duffy et al. |
| 2012/0022633 A1 | 1/2012 | Olson et al. |
| 2012/0022640 A1 | 1/2012 | Gross et al. |
| 2012/0035712 A1 | 2/2012 | Maisano et al. |
| 2012/0215236 A1 | 8/2012 | Matsunaga et al. |
| 2012/0232373 A1 | 9/2012 | Hallander et al. |
| 2012/0296349 A1 | 11/2012 | Smith et al. |
| 2013/0030522 A1 | 1/2013 | Rowe et al. |
| 2013/0325115 A1 | 12/2013 | Maisano et al. |
| 2015/0119979 A1 | 4/2015 | Maisano et al. |
| 2017/0000474 A1 | 1/2017 | Maisano et al. |
| 2019/0069991 A1 * | 3/2019 | Metchik .................. A61F 2/246 |

FOREIGN PATENT DOCUMENTS

| | | |
|---|---|---|
| WO | 9205093 A1 | 4/1992 |
| WO | 2005021063 A2 | 3/2005 |
| WO | 2005102194 A2 | 11/2005 |
| WO | 2006097931 A2 | 9/2006 |
| WO | 2008068756 A2 | 6/2008 |
| WO | 2009101617 A2 | 8/2009 |
| WO | 2010004546 A1 | 1/2010 |
| WO | 2010071494 A1 | 6/2010 |
| WO | 2010073246 A2 | 7/2010 |
| WO | 2010128502 A1 | 11/2010 |
| WO | 2010128503 A2 | 11/2010 |
| WO | 2011051942 A1 | 5/2011 |
| WO | 2011089601 A1 | 7/2011 |
| WO | 2011143263 A2 | 11/2011 |
| WO | 2012127309 A1 | 9/2012 |
| WO | 2017015632 A1 | 1/2017 |
| WO | 2017059426 A1 | 4/2017 |
| WO | 2017079153 A1 | 5/2017 |

* cited by examiner

HEART VALVE REPAIR IMPLANT FOR TREATING TRICUSPID REGURGITATION

CROSS-REFERENCE TO RELATED APPLICATIONS

This application claims the benefit of priority under 35 U.S.C. § 119 to U.S. Provisional Application Ser. No. 62/574,833, filed Oct. 20, 2017, the entirety of which is incorporated herein by reference.

TECHNICAL FIELD

The present disclosure pertains to medical devices and methods for manufacturing and/or using medical devices. More particularly, the present disclosure pertains to configurations of a heart valve repair implant.

BACKGROUND

A wide variety of intracorporeal medical devices have been developed for medical use, for example, surgical and/or intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. There is an ongoing need to provide alternative medical devices as well as alternative methods for manufacturing and/or using medical devices.

SUMMARY

In a first aspect, a heart valve repair implant may comprise a first implant section comprising: a first axial core, and a plurality of spines extending radially outward from the first axial core in an expanded configuration; a second implant section comprising: a second axial core configured to slide over the first axial core, and a mesh portion configured to extend radially outward from the second axial core in an expanded configuration; a third implant section comprising: a central tensioning element extending through the first axial core, and a plurality of arms extending radially outward from the central tensioning element and configured to extend axially between the plurality of spines and through the mesh portion; and a securement element disposed on the central tensioning element.

In addition or alternatively, and in a second aspect, the plurality of spines is circumferentially spaced apart from each other around the first axial core.

In addition or alternatively, and in a third aspect, the plurality of spines extends radially outward perpendicular to the first axial core in the expanded configuration.

In addition or alternatively, and in a fourth aspect, the mesh portion forms a flattened disc structure in the expanded configuration.

In addition or alternatively, and in a fifth aspect, the mesh portion is biased towards the expanded configuration.

In addition or alternatively, and in a sixth aspect, the mesh portion is self-biased towards the expanded configuration.

In addition or alternatively, and in a seventh aspect, the plurality of arms each includes a hook at a free end of its respective arm, each hook having a tip extending toward the first implant section.

In addition or alternatively, and in an eighth aspect, each hook is configured to engage the mesh portion when the central tensioning element is under tension.

In addition or alternatively, and in a ninth aspect, the securement element is configured to engage the first axial core or the second axial core to maintain the central tensioning element under tension.

In addition or alternatively, and in a tenth aspect, a heart valve repair system may comprise a first elongate shaft having a first implant section releasably attached at a distal end of the first elongate shaft, the first implant section comprising: a first axial core, and a plurality of spines extending radially outward from the first axial core in an expanded configuration; a second elongate shaft slidably disposed over the first elongate shaft, the second elongate shaft having a second implant section releasably attached at a distal end of the second elongate shaft, the second implant section comprising: a second axial core configured to slide over the first axial core, and a mesh portion configured to extend radially outward from the second axial core in an expanded configuration; and a third elongate shaft slidably disposed within the first elongate shaft, the third elongate shaft having a third implant section disposed proximate a distal end of the third elongate shaft, the third implant section comprising: a central tensioning element extending through the first axial core, and a plurality of arms extending radially outward from the central tensioning element and configured to extend axially between the plurality of spines and through the mesh portion.

In addition or alternatively, and in an eleventh aspect, the first elongate shaft is threadably attached to the first axial core.

In addition or alternatively, and in a twelfth aspect, the second elongate shaft is threadably attached to the second axial core.

In addition or alternatively, and in a thirteenth aspect, the heart valve repair system may further comprise a delivery catheter having a lumen extending from a proximal end to a distal end, wherein the delivery catheter is sized and configured to percutaneously navigate to a defective heart valve for delivery of the first implant section, the second implant section, and the third implant section to the defective heart valve.

In addition or alternatively, and in a fourteenth aspect, the plurality of spines is disposed between the first elongate shaft and the delivery catheter in a collapsed delivery configuration.

In addition or alternatively, and in a fifteenth aspect, the mesh portion is disposed between the second elongate shaft and the delivery catheter in a collapsed delivery configuration.

In addition or alternatively, and in a sixteenth aspect, a heart valve repair implant for improving function of defective heart valve having a plurality of valve leaflets may comprise a first implant section comprising a plurality of spines extending radially outward from a first axial core in an expanded configuration; a second implant section comprising a mesh portion configured to extend radially outward from a second axial core in an expanded configuration, the second axial core being disposed around the first axial core; and a third implant section comprising a plurality of arms extending radially outward from a central tensioning element extending through the first axial core, the plurality of arms being configured to extend axially between the plurality of spines and through the mesh portion. The first implant section may be configured to be positioned on a downstream side of the plurality of valve leaflets, the second implant section may be configured to be positioned on an upstream side of the plurality of valve leaflets, and relative axial translation of the first implant section and the second implant section towards each other squeezes at least a portion of each valve leaflet between the first implant section and the second implant section.

In addition or alternatively, and in a seventeenth aspect, the plurality of arms is configured to pierce and extend through the plurality of valve leaflets squeezed between the first implant section and the second implant section.

In addition or alternatively, and in an eighteenth aspect, when tension is applied to the central tensioning element, free ends of the plurality of arms engage the second implant section and the plurality of arms engages the first axial core such that the second implant section and the first implant section are urged towards each other.

In addition or alternatively, and in a nineteenth aspect, the mesh portion defines an outer perimeter having a substantially circular shape in the expanded configuration.

In addition or alternatively, and in a twentieth aspect, the mesh portion defines an outer perimeter having a multi-lobed shape in the expanded configuration.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
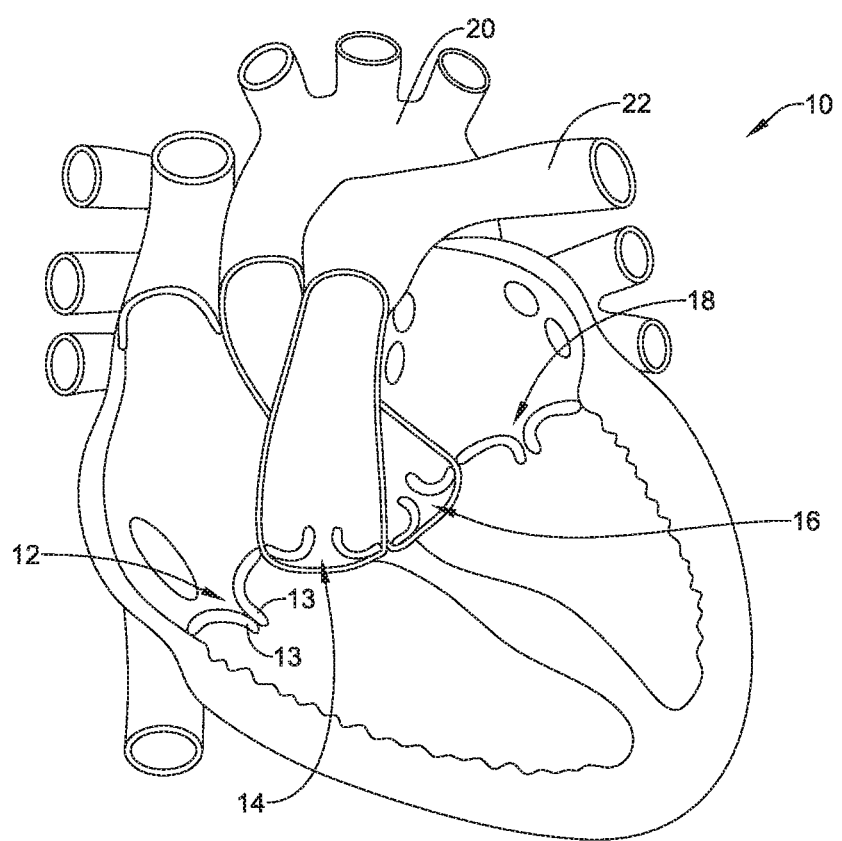
FIG. 1 illustrates selected elements of an example heart.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to correspond to a measurement of a stated of identified dimension. The term "maximum extent" may be understood to mean a greatest measurement of a stated or identified dimension, while the term "minimum extent" may be understood to mean a smallest measurement of a stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, a "maximum extent" may be considered a greatest possible dimension measured according to the intended usage. Alternatively, a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Diseases and/or medical conditions that impact the cardiovascular system are prevalent throughout the world. Traditionally, treatment of the cardiovascular system was often conducted by directly accessing the impacted part of the system. For example, treatment of a blockage in one or more of the coronary arteries was traditionally treated using coronary artery bypass surgery. As can be readily appreciated, such therapies are rather invasive to the patient and require significant recovery times and/or treatments. More recently, less invasive therapies have been developed, for example, where a blocked coronary artery could be accessed and treated via a percutaneous catheter (e.g., angioplasty). Such therapies have gained wide acceptance among patients and clinicians.

Some mammalian hearts (e.g., human, etc.) include four heart valves: a tricuspid valve 12, a pulmonary valve 14, an aortic valve 16, and a mitral valve 18, as seen in an example heart 10 illustrated in FIG. 1. The purpose of the heart valves is to allow blood to flow through the heart 10 and from the heart 10 into the major blood vessels connected to the heart 10, such as the aorta 20 and the pulmonary artery 22, for example. Each of the four heart valves may include a plurality of valve leaflets. For example, the tricuspid valve 12 may include a plurality of valve leaflets 13 (e.g., two valve leaflets, three valve leaflets, etc.). A normal tricuspid valve 12 typically has three valve leaflets 13, although other configurations are known to occur. In a normally functioning heart valve, the valve leaflets permit blood to pass or flow downstream through the heart valve (e.g., from an atrium to a ventricle, from a ventricle to an artery, etc.) when the heart valve is open, and when the heart valve is closed, the valve leaflets prevent blood from passing or flowing back upstream through the heart valve (e.g., from a ventricle to an atrium, etc.).

Some relatively common medical conditions may include or be the result of inefficiency, ineffectiveness, or complete failure of one or more of the valves within the heart. For example, when regurgitation (e.g., mitral regurgitation, tricuspid regurgitation, etc.) occurs, a heart valve (e.g., the mitral valve 18, the tricuspid valve 12, etc.) fails to open and/or close properly such that blood is permitted to pass or flow back upstream through the heart valve (e.g., from a ventricle to an atrium, etc.) during systole. In some cases, the defective heart valve may have leaflets that may not close, or may not be capable of closing, completely during systole.

Treatment of defective heart valves poses other challenges in that the treatment often requires the repair or outright replacement of the defective valve, and/or the treatment must be performed surgically. Such therapies may be highly invasive to the patient. Disclosed herein are medical devices that may be used within a portion of the cardiovascular system in order to diagnose, treat, and/or repair the system. The medical devices disclosed herein may include a heart valve repair implant, and may reduce and/or treat the occurrence of defects such as (but not limited to) regurgitation, leaflet prolapse, and/or valve stenosis. In addition, the devices disclosed herein may deliver the heart valve repair implant percutaneously and, thus, may be much less invasive to the patient, although other approaches may also be used. In an alternative method, the devices disclosed herein may be used with open-heart surgical methods in patients deemed unsuitable for percutaneous treatment. The devices disclosed herein may also provide a number of additional desirable features and benefits as described in more detail below. For the purpose of this disclosure, the discussion below is directed treating a defective tricuspid valve 12 and will be so described in the interest of brevity. This, however, is not intended to be limiting as the skilled person will recognize that the following discussion may also apply to other heart valves with no or minimal changes to the structure and/or scope of the disclosure.

Figure 2:
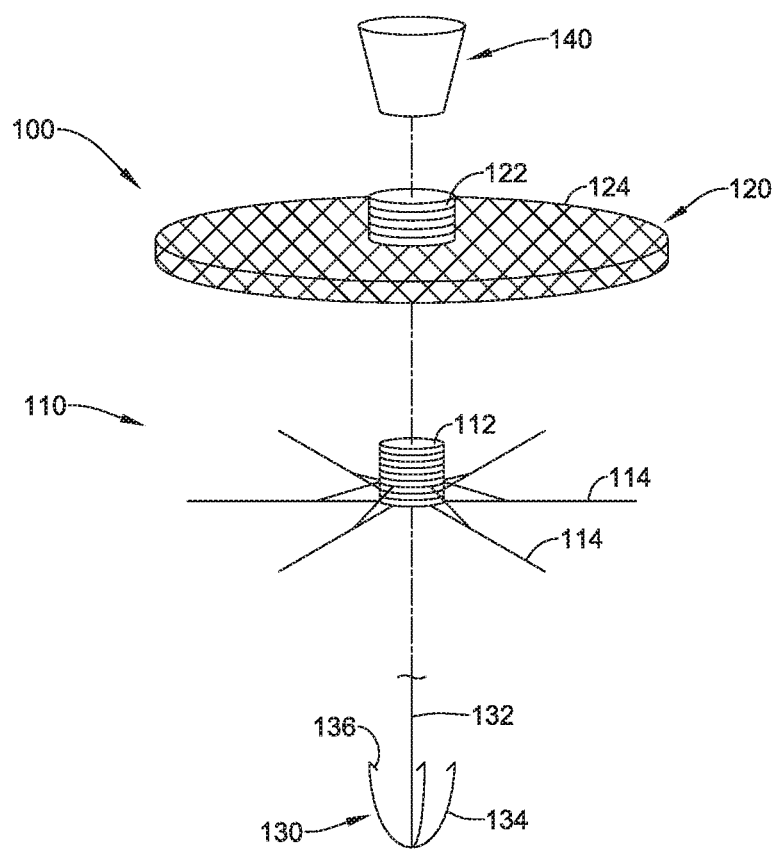
FIG. 2 is an exploded view illustrating a heart valve repair implant.

FIG. 2 illustrates aspects of an example heart valve repair implant 100. The heart valve repair implant 100 may include first implant section 110, a second implant section 120, a third implant section 130, and/or a securement element 140. The heart valve repair implant 100 may be configured to implantation within a heart valve (e.g., the tricuspid valve 12, etc.) to bind the tips of the valve leaflets together to improve coaptation of the valve leaflets during systole. During diastole, the valve leaflets may form a plurality of openings through which blood may pass while still being bound together at the tips of the valve leaflets.

In some embodiments, the first implant section 110 may comprise a first axial core 112 and/or a plurality of spines 114 extending radially outward from the first axial core 112. The plurality of spines 114 may be flexibly and/or pivotably attached to a distal portion of the first axial core 112 and/or at a distal end of the first axial core 112. The plurality of spines 114 may be configured to shift from a collapsed delivery configuration to an expanded configuration. In some embodiments, the plurality of spines 114 may be biased toward the expanded configuration. In some embodiments, the plurality of spines 114 may be self-biased toward the expanded configuration. A majority of a length of the plurality of spines 114 may extend generally parallel to the first axial core 112 in the collapsed delivery configuration. In at least some embodiments, the plurality of spines 114 extends radially outward substantially perpendicular to the first axial core 112 in the expanded configuration. The plurality of spines 114 may be circumferentially spaced apart from each other around the first axial core 112. In some embodiments, the plurality of spines 114 may form a generally disc-like structure in the expanded configuration. The plurality of spines 114 may include 2 spines, 3 spines, 4 spines, 5 spines, 6 spines, 7 spines, 8 spines, 9 spines, 10 spines, or another suitable quantity of spines. In some embodiments, the plurality of spines 114 may each include at least one support strut connecting its respective spine to the first axial core 112, the at least one support strut being configured to limit distal movement and/or extension of the plurality of spines 114. For example, in some embodiments, the plurality of spines 114 and/or the at least one support strut may be incapable of pivoting, flexing, and/or extending distally past a substantially horizontal configuration and/or perpendicular to the first axial core 112. Some suitable but non-limiting materials for the first implant section 110, for example metallic materials, polymer materials, composite materials, etc., are described below.

In some embodiments, the second implant section 120 may comprise a second axial core 122 and/or a mesh portion 124 extending radially outward from the second axial core 122. The second axial core 122 may be configured to slide and/or axially translate over and/or around the first axial core 112. The mesh portion 124 may be flexibly and/or pivotably attached to a distal portion of the second axial core 122 and/or at a distal end of the second axial core 122. The mesh portion 124 may be configured to shift from a collapsed delivery configuration to an expanded configuration. In some embodiments, the mesh portion 124 may be biased toward the expanded configuration. In some embodiments, the mesh portion 124 may be self-biased toward the expanded configuration. In some embodiments, a majority of a length of the mesh portion 124 may extend generally parallel to the second axial core 122 in the collapsed delivery configuration. In some embodiments, the mesh portion 124 may be configured to axially shorten and/or radially expand when shifting from the delivery configuration to the expanded configuration. In at least some embodiments, the mesh portion 124 extends radially outward substantially perpendicular to the second axial core 122 in the expanded configuration. In some embodiments, the mesh portion 124 may form a generally flattened disc structure in the expanded configuration. In some embodiments, the mesh portion 124 may include at least one support strut connecting to the second axial core 122, the at least one support strut being configured to limit distal movement and/or extension of the mesh portion 124. For example, in some embodiments, the mesh portion 124 and/or the at least one support strut may be incapable of pivoting, flexing, and/or extending distally past a substantially horizontal configuration and/or perpendicular to the second axial core 122. In at least some embodiments, the mesh portion 124 of the second implant section 120 may be formed as a loose or sparse network of filaments or a braid capable of permitting blood flow therethrough. Some suitable but non-limiting materials for the second implant section 120, for example metallic materials, polymer materials, composite materials, etc., are described below.

In some embodiments, the third implant section 130 may comprise a central tensioning element 132 and/or a plurality of arms 134 extending radially outward from the central tensioning element 132. The central tensioning element 132 may extend through the first axial core 112 of the first implant section 110 and/or the second axial core 122 of the second implant section 120. The plurality of arms 134 may be flexibly and/or pivotably attached to a distal end of the central tensioning element 132. The plurality of arms 134 may be configured to shift from a collapsed delivery configuration to an expanded configuration. In some embodiments, the plurality of arms 134 may be biased toward the expanded configuration. In some embodiments, the plurality of arms 134 may be self-biased toward the expanded configuration. A majority of a length of the plurality of arms 134 may extend generally parallel to the central tensioning element 132 in the collapsed delivery configuration. In some embodiments, the plurality of arms 134 may be configured to extend axially between the plurality of spines 114 of the first implant section 110 and/or through the mesh portion 124 of the second implant section 120 in the expanded configuration.

The plurality of arms 134 may be circumferentially spaced apart from each other around the central tensioning element 132. In at least some embodiments, each of the plurality of arms 134 extends radially outward at an acute and/or oblique angle from the central tensioning element 132 to a free end in the expanded configuration. In some embodiments, the plurality of arms 134 may form a generally conical or pyramidal structure in the expanded configuration, wherein a distal end of each of the plurality of arms 134 is attached and/or connected at and/or to the distal end of the central tensioning element 132, and the free end of each of the plurality of arms 134 is radially spaced away from the central tensioning element 132. The plurality of arms 134 may each include a hook 136 at the free end of its respective arm, each hook 136 having a tip extending toward the distal end of its respective arm, toward the distal end of the central tensioning element 132, and/or toward the first implant section 110.

In some embodiments, the plurality of arms 134 may include 2 arms, 3 arms, 4 arms, 5 arms, 6 arms, 7 arms, 8 arms, 9 arms, 10 arms, or another suitable quantity of arms. In some embodiments, the plurality of arms 134 may each include at least one support strut connecting its respective arm to the central tensioning element 132, the at least one support strut being configured to limit radially outward movement and/or extension of the free end(s) of the plurality of arms 134. For example, in some embodiments, the plurality of arms 134 and/or the at least one support strut may be incapable of pivoting, flexing, and/or extending radially outward past a desired angle relative to the central tensioning element 132—for example, 15 degrees, 20 degrees, 30 degrees, 35 degrees, 45 degrees, 60 degrees, etc. Some suitable but non-limiting materials for the third implant section 130, for example metallic materials, polymer materials, composite materials, etc., are described below.

The heart valve repair implant 100 may include the securement element 140 disposed on the central tensioning element 132. The securement element 140 may include a proximal end, a distal end, and a side surface extending between the proximal end and the distal end. In some embodiments, the securement element 140 may be selectively slidable on, along, and/or over the central tensioning element 132. In some embodiments, the securement element 140 may be configured to be fixedly attached and/or secured to and/or along the central tensioning element 132 such that and/or wherein axial movement of the securement element 140 along the central tensioning element 132 is prevented. In some embodiments, the securement element 140 may be tapered, stepped, angled, etc. along the side surface between the proximal end and the distal end. In some embodiments, the distal end of the securement element 140 may have an outer extent sized and configured to fit and/or be disposed within the first axial core 112 and/or the second axial core 122. In some embodiments, the proximal end of the securement element 140 may be larger than and/or have a greater outer extent than the distal end of the securement element 140. For example, in some embodiments, the proximal end of the securement element 140 may have an outer extent greater than the first axial core 112 and/or the second axial core 122, such that the entire securement element 140 is prevented from completely entering into and/or passing through the first axial core 112 and/or the second axial core 122. Other configurations of the securement element 140 are also contemplated. Some suitable but non-limiting materials for the securement element 140, for example metallic materials, polymer materials, composite materials, etc., are described below.

Figure 3:
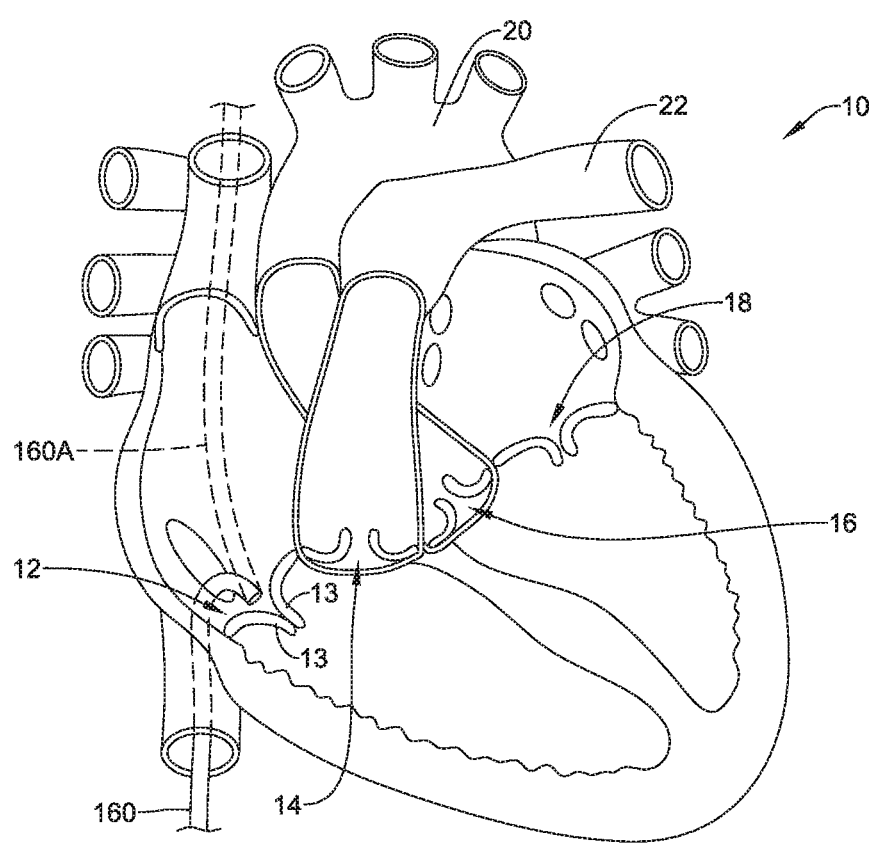
FIGS. 3-12 illustrate aspects of a heart valve repair system and a method of delivering the heart valve repair implant to a defective tricuspid valve.

In some embodiments, a heart valve repair system may include the heart valve repair implant 100 described herein. In some embodiments, the heart valve repair system may further comprise a delivery catheter 160 having a lumen extending from a proximal end to a distal end, wherein the delivery catheter 160 is sized and configured to percutaneously navigate to a defective heart valve (e.g., the tricuspid valve 12, etc.) for delivery of the first implant section 110, the second implant section 120, and the third implant section 130 to the defective heart valve (e.g., the tricuspid valve 12, etc.), as seen in FIG. 3 for example. In some embodiments, the delivery catheter 160 may be navigated to the heart 10 via the inferior vena cava. In an alternative approach, a delivery catheter 160A may be navigated to the heart 10 via the superior vena cava. Other alternative approaches and/or delivery methods may be used, including but not limited to, an aortic approach and/or a surgical delivery.

Figure 4:
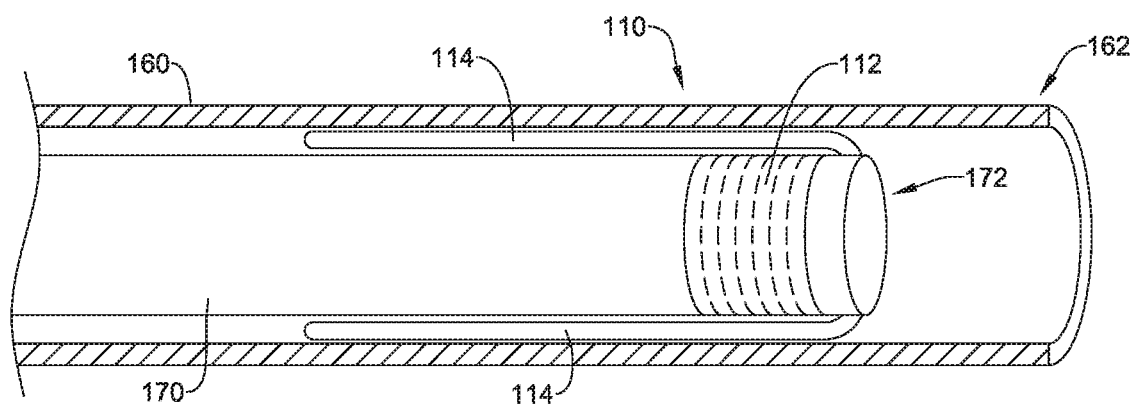

In some embodiments, the heart valve repair system may comprise a first elongate shaft 170 having the first implant section 110 releasably attached at a distal end 172 of the first elongate shaft 170, as seen in FIG. 4 for example. The first axial core 112 of the first implant section 110 may have and/or include external threads configured to engage internal threads formed in the distal end 172 of the first elongate shaft 170. The first elongate shaft 170 may be threadably attached to the first axial core 112 of the first implant section 110. Other means of releasably attaching the first implant section 110 to the distal end 172 of the first elongate shaft 170 are also contemplated. During delivery, the first implant section 110 may be disposed within a distal end 162 of the delivery catheter 160 in the collapsed delivery configuration as the delivery catheter 160 is navigated to the defective heart valve (e.g., the tricuspid valve 12, etc.), and then the first implant section 110 may be deployed out of the distal end 162 of the delivery catheter 160 via relative axial translation of the first elongate shaft 170 and the delivery catheter 160. In some embodiments, the first implant section 110 may be advanced through the delivery catheter 160 in the collapsed delivery configuration, by axially translating the first elongate shaft 170 within and relative to the delivery catheter 160, after the delivery catheter 160 has been navigated to the defective heart valve (e.g., the tricuspid valve 12, etc.). The plurality of spines 114 may be disposed between an outer surface of the first elongate shaft 170 and an inner surface of the delivery catheter 160 in the collapsed delivery configuration. In at least some embodiments, the plurality of spines 114 may extend proximally from the first axial core 112 and/or the distal end 172 of the first elongate shaft 170 in the collapsed delivery configuration.

Figure 5:
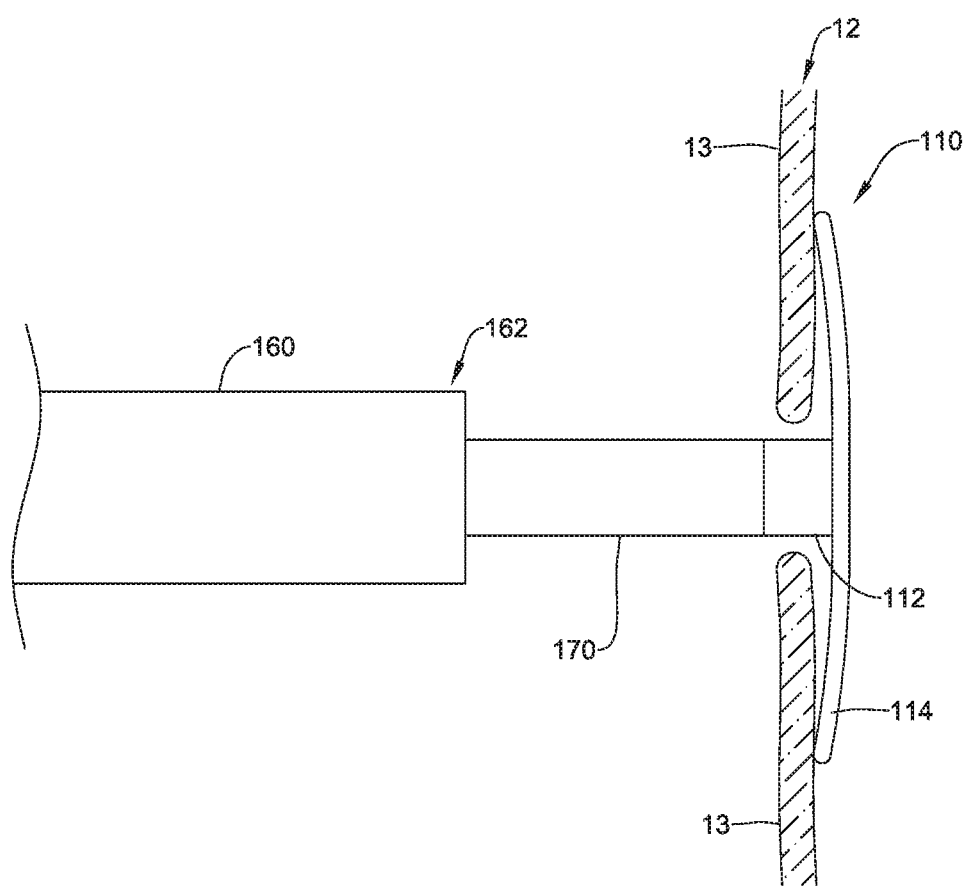

The first implant section 110 may be axially translated out of the distal end 162 of the delivery catheter 160 within the defective heart valve (e.g., the tricuspid valve 12, etc.). In some embodiments, the first implant section 110 may be configured to be positioned on a downstream side of the plurality of valve leaflets 13 in the expanded configuration, as seen in FIG. 5 for example. In some embodiments, the first implant section 110 may be configured to assume and/or may define a concave shape facing towards the plurality of valve leaflets 13 in the expanded configuration, wherein free ends of the plurality of spines 114 of the first implant section 110 may contact the downstream side of the plurality of valve leaflets 13. In at least some embodiments, the first axial core 112 may extend through the defective heart valve (e.g., the tricuspid valve 12, etc.) between the plurality of valve leaflets 13. In the expanded configuration, the first implant section 110 having the plurality of spines 114 may limit or prevent entanglement with and/or displacement of the chordae connecting the papillary muscles to the plurality of valve leaflets 13. In some embodiments, it may be necessary and/or desirable to recapture and/or reposition the plurality of spines 114 of the first implant section 110, before moving on with the procedure. As such, the delivery catheter 160 may be advanced and/or the first elongate shaft 170 may be retracted axially relative to each other to translate the first implant section 110 back inside the distal end 162 of the delivery catheter 160, the delivery catheter 160 may be repositioned as desired, and the deployment process may be repeated to axially translate the first implant section 110 out of the distal end 162 of the delivery catheter 160 within the defective heart valve (e.g., the tricuspid valve 12, etc.). At this point in the deployment process/method, the first elongate shaft 170 and the first implant section 110 may be held substantially still and/or in a static position within and/or relative to the defective heart valve (e.g., the tricuspid valve 12, etc.) and/or downstream of the plurality of valve leaflets 13.

Figure 6:
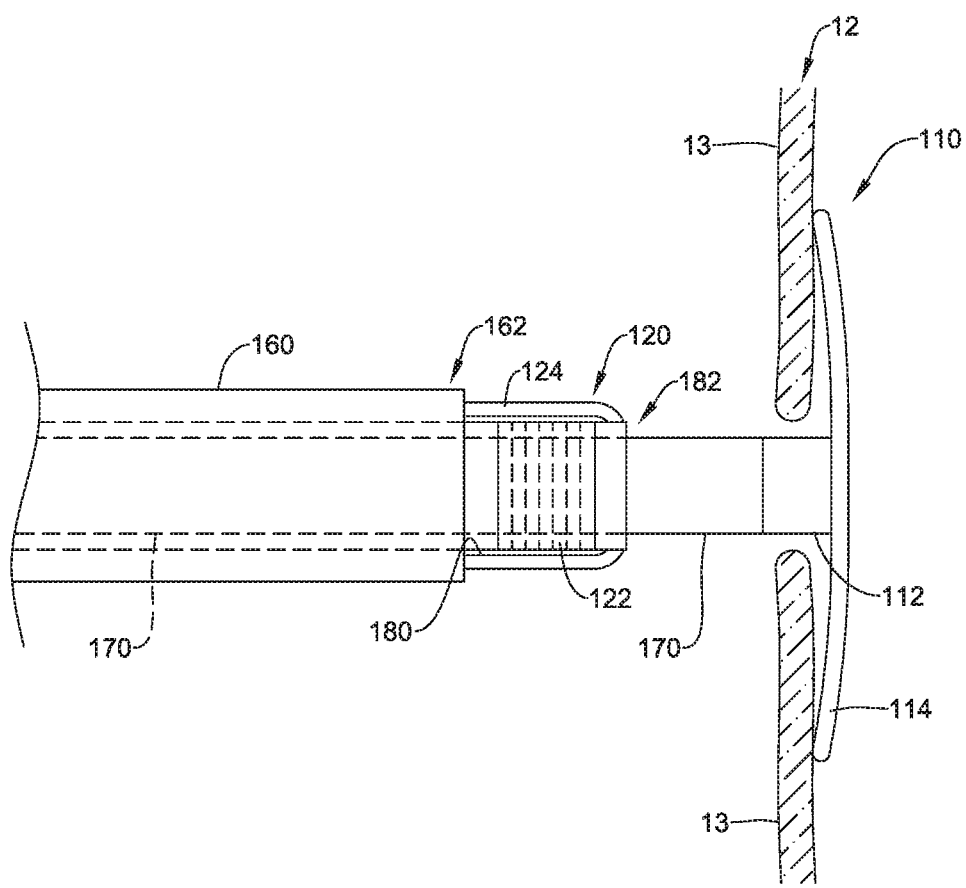

In some embodiments, the heart valve repair system may comprise a second elongate shaft 180 slidably disposed over the first elongate shaft 170, the second elongate shaft 180 having the second implant section 120 releasably attached at a distal end 182 of the second elongate shaft 180, as seen in FIG. 6 for example. The second axial core 122 of the second implant section 120 may have and/or include external threads configured to engage internal threads formed in the distal end 182 of the second elongate shaft 180. The second elongate shaft 180 may be threadably attached to the second axial core 122 of the second implant section 120. Other means of releasably attaching the second implant section 120 to the distal end 182 of the second elongate shaft 180 are also contemplated. During delivery, the second implant section 120 may be disposed within the distal end 162 of the delivery catheter 160 proximal to the first implant section 110 in the collapsed delivery configuration as the delivery catheter 160 is navigated to the defective heart valve (e.g., the tricuspid valve 12, etc.), and then the second implant section 120 may be deployed out of the distal end 162 of the delivery catheter 160 via relative axial translation of the second elongate shaft 180 and the delivery catheter 160 after the first implant section 110 has been deployed. In some embodiments, the second implant section 120 may be advanced through the delivery catheter 160 in the collapsed delivery configuration, by axially translating the second elongate shaft 180 within and relative to the delivery catheter 160, after the delivery catheter 160 has been navigated to the defective heart valve (e.g., the tricuspid valve 12, etc.) and/or the first implant section 110 has been deployed.

In some embodiments, the mesh portion 124 may be disposed between an outer surface of the second elongate shaft 180 and the inner surface of the delivery catheter 160 in the collapsed delivery configuration. In at least some embodiments, the mesh portion 124 may extend proximally from the second axial core 122 and/or the distal end 182 of the second elongate shaft 180 in the collapsed delivery configuration. In some embodiments, the mesh portion 124 may be axially elongated in the collapsed delivery configuration and may axially shorten, wherein a proximal end of the mesh portion 124 proximate the second elongate shaft 180 and a distal end of the mesh portion 124 proximate the second elongate shaft 180 axially translate relative to each other, when shifting to the expanded configuration. For example, when shifting to the expanded configuration, a middle portion of the mesh portion 124 disposed adjacent to the second elongate shaft 180 may translate radially outward from the second elongate shaft 180 to form an outer perimeter or outer extent of the mesh portion in the expanded configuration.

Figure 7:
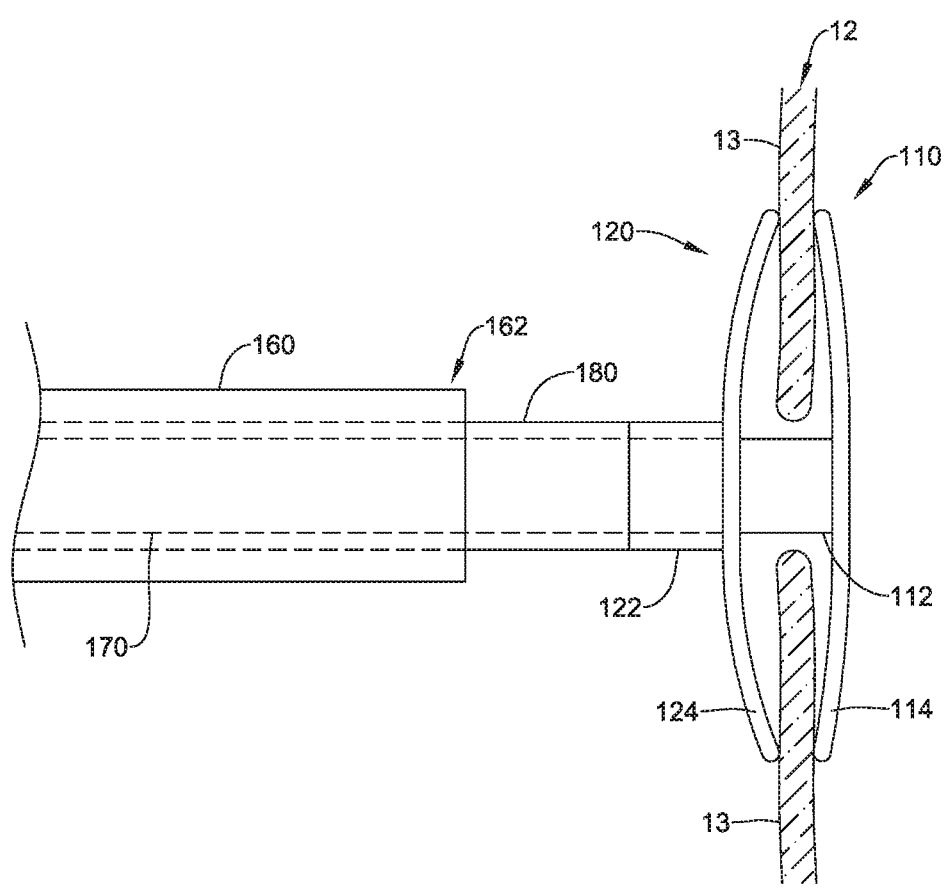

The second implant section 120 may be axially translated out of the distal end 162 of the delivery catheter 160 within the defective heart valve (e.g., the tricuspid valve 12, etc.). In some embodiments, the second implant section 120 may be configured to be positioned on an upstream side of the plurality of valve leaflets 13 in the expanded configuration, as seen in FIG. 7 for example. In some embodiments, the second implant section 120 may be configured to assume and/or may define a concave shape facing towards the plurality of valve leaflets 13 in the expanded configuration, wherein an outer perimeter and/or edge of the mesh portion 124 of the second implant section 120 may contact the upstream side of the plurality of valve leaflets 13. In some embodiments, the concave shape of the first implant section 110 may be opposite and/or face towards the concave shape of the second implant section 120. In at least some embodiments, the second axial core 122 may be configured to be positioned at least partially over the first axial core 112. The first elongate shaft 170 and the first implant section 110 may continue to be held substantially still and/or in a static position within and/or relative to the defective heart valve (e.g., the tricuspid valve 12, etc.) and/or downstream of the plurality of valve leaflets 13 during deployment of the second implant section 120 upstream of the plurality of valve leaflets 13. In some embodiments, during this process, the defective heart valve (e.g., the tricuspid valve 12, etc.) may continue to function "normally", or as normally as the defective heart valve was functioning prior to the procedure. In some embodiments, it may be necessary and/or desirable to recapture and/or reposition the mesh portion 124 of the second implant section 120, before moving on with the procedure. As such, the delivery catheter 160 may be advanced and/or the second elongate shaft 180 may be retracted axially relative to each other to translate the second implant section 120 back inside the distal end 162 of the delivery catheter 160, the delivery catheter 160 may be repositioned as desired, and the deployment process may be repeated to axially translate the second implant section 120 out of the distal end 162 of the delivery catheter 160 within the defective heart valve (e.g., the tricuspid valve 12, etc.).

Figure 8:
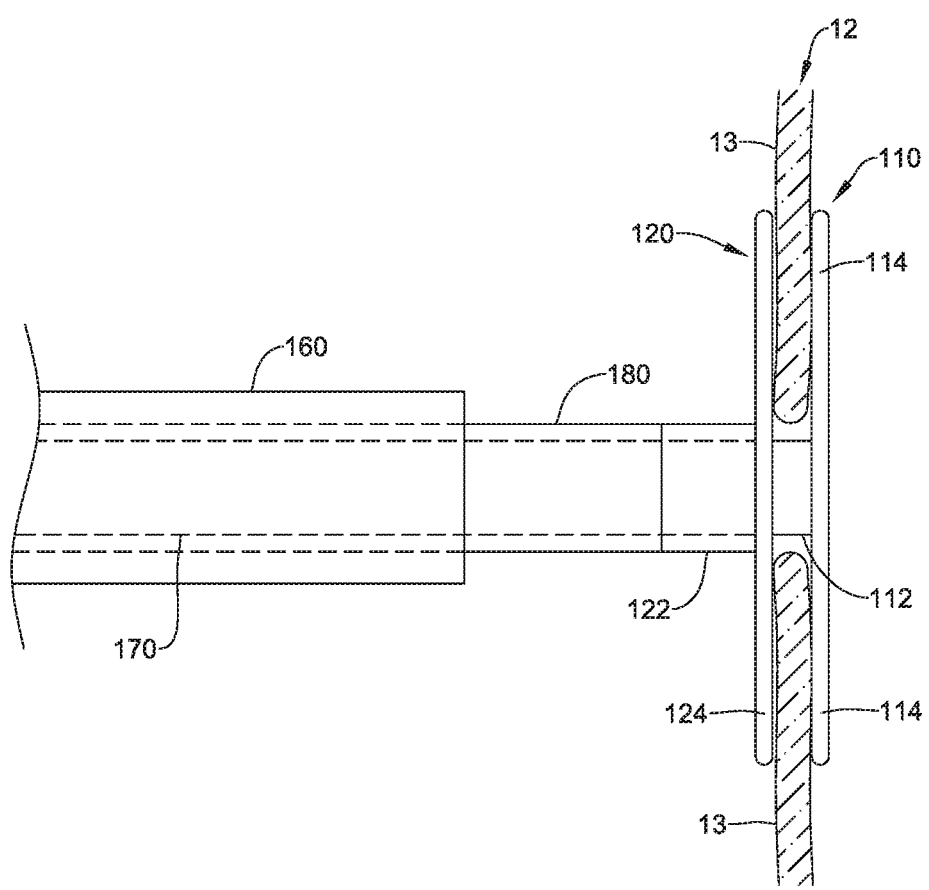

Next, after deployment of the second implant section 120 upstream of the plurality of valve leaflets 13, the second elongate shaft 180 and the second implant section 120 may be axially translated toward the plurality of valve leaflets 13 and/or the first implant section 110, which may continue to be held substantially still and/or in a static position within and/or relative to the defective heart valve (e.g., the tricuspid valve 12, etc.) and/or downstream of the plurality of valve leaflets 13, as seen in FIG. 8 for example. The second axial core 122 may be axially translated relative to and at least partially over the first axial core 112, as the first elongate shaft 170 extends through the delivery catheter 160, the second elongate shaft 180, and the second axial core 122. Relative axial translation of the first implant section 110 and the second implant section 120 towards each other while positioned within the defective heart valve (e.g., the tricuspid valve 12, etc.) may squeeze at least a portion of each valve leaflet 13 between the first implant section 110 and the second implant section 120. Relative axial translation of the first implant section 110 and the second implant section 120 towards each other while positioned within the defective heart valve (e.g., the tricuspid valve 12, etc.) may also flatten and/or reduce the concavity of the first implant section 110 and the second implant section 120 as at least a portion of each valve leaflet 13 is squeezed between the first implant section 110 and the second implant section 120, as shown in FIG. 8.

In an alternative embodiment, the first implant section 110 and the second implant section 120 could be combined and may extend radially outward from a single axial core. Similarly, the first implant section 110 and the second implant section 120 may be releasably attached to a single elongate shaft, and the first implant section 110 and the second implant section 120 may be slidably disposed within the delivery sheath 160. When disposed within the delivery sheath 160, the plurality of spines 114 may extend distally from the single axial core in the collapsed delivery configuration and/or within the delivery sheath 160, and the mesh portion 124 may extend proximally from the single axial core in the collapsed delivery configuration and/or within the delivery sheath 160. Deployment may be similar to that described above. As the single elongate shaft is translated axially relative to the distal end 162 of the delivery sheath 160, the plurality of spines 114 of the first implant section 110 may be positioned on the downstream side of the plurality of valve leaflets 13 and may extend radially outward in the expanded configuration. The delivery sheath 160 may then be retracted from the first implant section 110 and/or the single axial core, which is positioned within the defective heart valve (e.g., the tricuspid valve 12, etc.), to deploy the mesh portion 124 of the second implant section 120 on the upstream side of the plurality of valve leaflets 13 in the expanded configuration. The single axial core may be sized and configured to correspond to the plurality of valve leaflets 13 such that the first implant section 110 and the second implant section 120 substantially squeeze and/or capture at least a portion of each valve leaflet 13 between the first implant section 110 and the second implant section 120.

Figure 9:
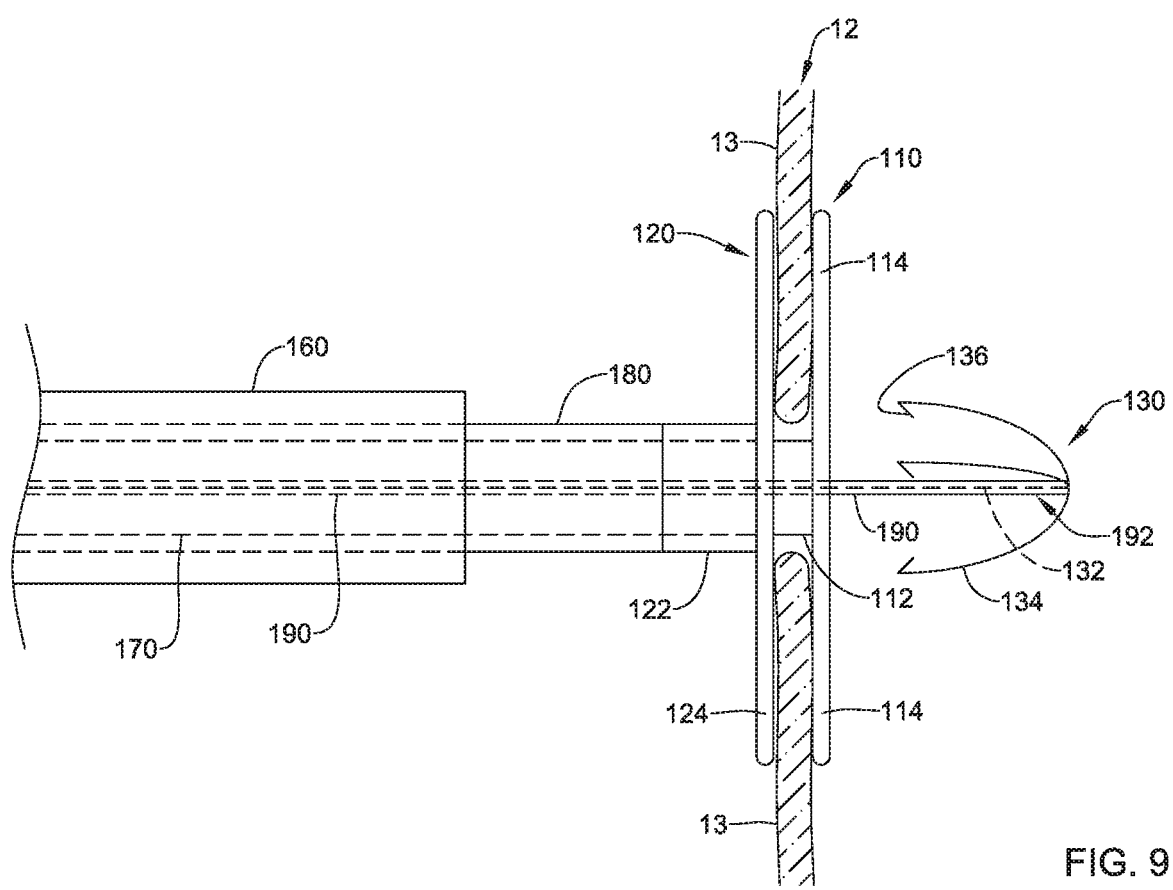

In some embodiments, the heart valve repair system may comprise a third elongate shaft 190 slidably disposed within the first elongate shaft 170, the third elongate shaft 190 having the third implant section 130 disposed proximate a distal end 192 of the third elongate shaft 190, as seen in FIG. 9 for example. During delivery, the third implant section 130 may be disposed within the distal end 172 of the first elongate shaft 170 in the collapsed delivery configuration as the delivery catheter 160 and/or the first elongate shaft 170 is navigated to the defective heart valve (e.g., the tricuspid valve 12, etc.). In at least some embodiments, the plurality of arms 134 may be disposed between an outer surface of the third elongate shaft 190 and an inner surface of the first elongate shaft 170 in the collapsed delivery configuration. In at least some embodiments, the plurality of arms 134 may extend proximally from the central tensioning element 132 and/or the distal end 192 of the third elongate shaft 190 in the collapsed delivery configuration. After squeezing at least a portion of each valve leaflet 13 between the first implant section 110 and the second implant section 120, the first elongate shaft 170, the first implant section 110, the second elongate shaft 180, and/or the second implant section 120 may be held substantially still and/or in a static position within and/or relative to the defective heart valve (e.g., the tricuspid valve 12, etc.), and the third elongate shaft 190 and/or the third implant section 130 may be advanced distally past the first implant section 110 on the downstream side of the plurality of valve leaflets 13 to deploy the plurality of arms 134.

Figure 10:
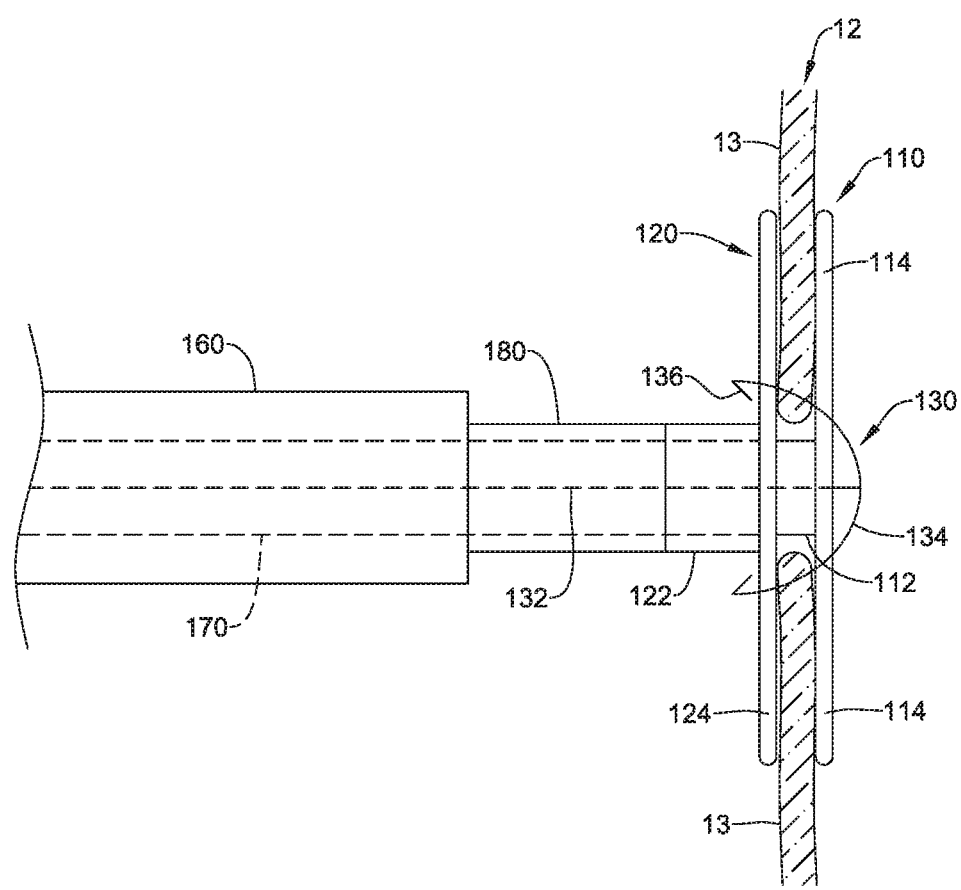

After deployment and radial expansion and/or extension, the plurality of arms 134 may be configured to pierce and/or extend through the plurality of valve leaflets 13 squeezed between the first implant section 110 and the second implant section 120. For example, in some embodiments, at a location where the hook 136 at the free end of each arm 134 turns and extends toward the tip (e.g., distally and/or toward the distal end 192 of the third elongate shaft 190), the hook 136 may form a piercing structure such as a point, an edge, etc. capable of cleanly piercing tissue of the plurality of valve leaflets 13 without tearing said tissue. Next, the third elongate shaft 190 and/or the central tensioning element 132 and the plurality of arms 134 may be withdrawn proximally to pull the hook 136 at the free end of each of the plurality of arms 134 between the plurality of spines 114 of the first implant section 110, through the tissue of the plurality of valve leaflets 13, and through the mesh portion 124 of the second implant section 120, as shown in FIG. 10. In some embodiments, the delivery catheter 160 may be advanced distally against and/or into engagement with the mesh portion 124 of the second implant section 120 as and/or immediately before the plurality of arms 134 is withdrawn proximally to pull the hook 136 at the free end of each of the plurality of arms 134 between the plurality of spines 114 of the first implant section 110, through the tissue of the plurality of valve leaflets 13, and through the mesh portion 124 of the second implant section 120. In some embodiments, the third elongate shaft 190 may be withdrawn clear of the heart valve repair implant 100 and/or completely out of the delivery catheter 160, the first elongate shaft 170, and/or the second elongate shaft 180.

Each hook 136 at the free end of each of the plurality of arms 134 may be configured to engage with the mesh portion 124 of the second implant section 120 when the central tensioning element 132 is under tension. As such, after pulling the hook 136 at the free end of each of the plurality of arms 134 between the plurality of spines 114 of the first implant section 110, through the tissue of the plurality of valve leaflets 13, and through the mesh portion 124 of the second implant section 120 to the position shown in FIG. 10, the first elongate shaft 170, the first implant section 110, the second elongate shaft 180, and/or the second implant section 120 may be held substantially still and/or in a static position within and/or relative to the defective heart valve (e.g., the tricuspid valve 12, etc.) as tension is applied to the central tensioning element 132 (for example, by pulling the central tensioning element 132 proximally relative to the first elongate shaft 170, the first implant section 110, the second elongate shaft 180, and/or the second implant section 120).

Figure 11:
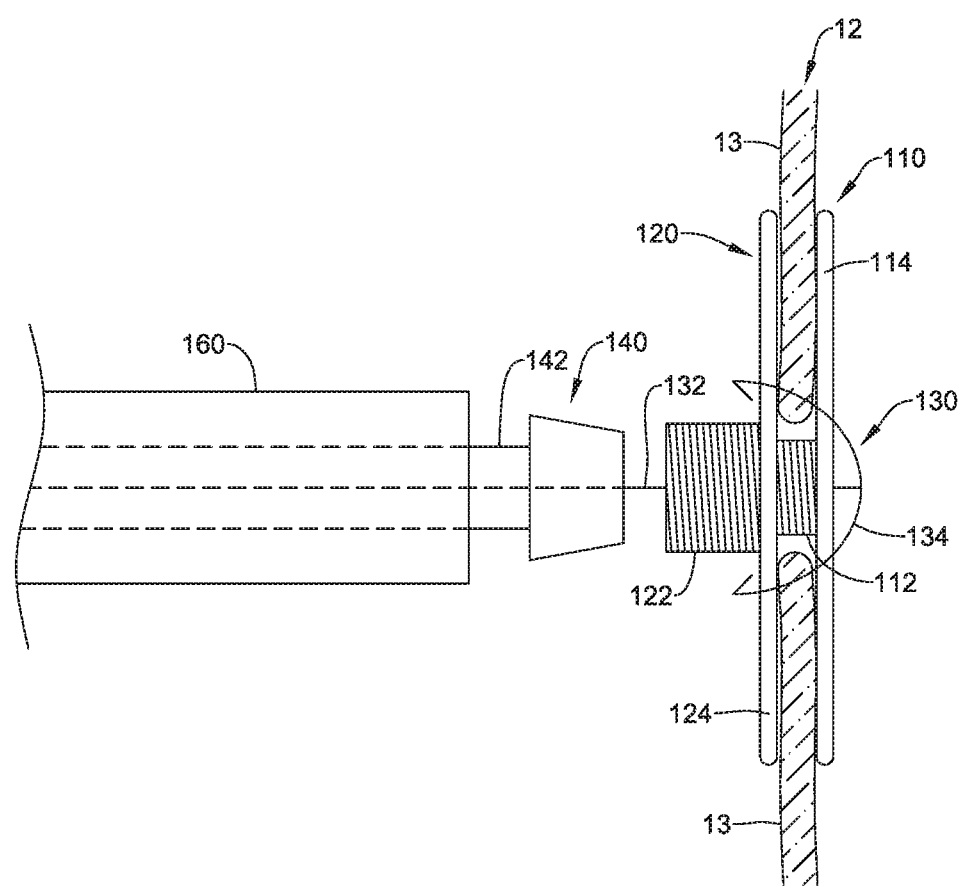

As seen in FIG. 11, when the first implant section 110, the second implant section 120, and the third implant section 130 have been deployed within a defective heart valve (e.g., the tricuspid valve 12, etc.), the first elongate shaft 170 may be disconnected from the first axial core 112 of the first implant section 110 and retracted through the delivery catheter 160. Additionally, in at least some embodiments, the second elongate shaft 180 may be disconnected from the second axial core 122 of the second implant section 120 and retracted through the delivery catheter 160. Similarly, the third elongate shaft 190 may be retracted through the delivery catheter 160. The securement element 140, disposed at a distal end of a fourth elongate shaft 142, may be advanced through the delivery catheter 160 over and/or along the central tensioning element 132 to a position adjacent the first axial core 112 and/or the second axial core 122. The fourth elongate shaft 142 may include a lumen extending through the fourth elongate shaft 142 configured to slidably receive the central tensioning element 132 such that the fourth elongate shaft 142 may be inserted and/or advanced over the central tensioning element 132. In some embodiments, the fourth elongate shaft 142 may be a pusher, a hypotube, a bar, or other suitable element for advancing the securement element 140 through the delivery catheter 160 to a position adjacent the first axial core 112 and/or the second axial core 122.

In some embodiments, the securement element 140 may be an expandable member configured to radially expand from a collapsed delivery configuration to a deployed or expanded configuration. For example, the securement element 140 may be configured for delivery within and/or through the first elongate shaft 170 and/or the second elongate shaft 180, wherein the securement element 140 is configured to expand radially outward after being deployed from the distal end 172 of the first elongate shaft 170 and/or the distal end 182 of the second elongate shaft 180.

Figure 12:
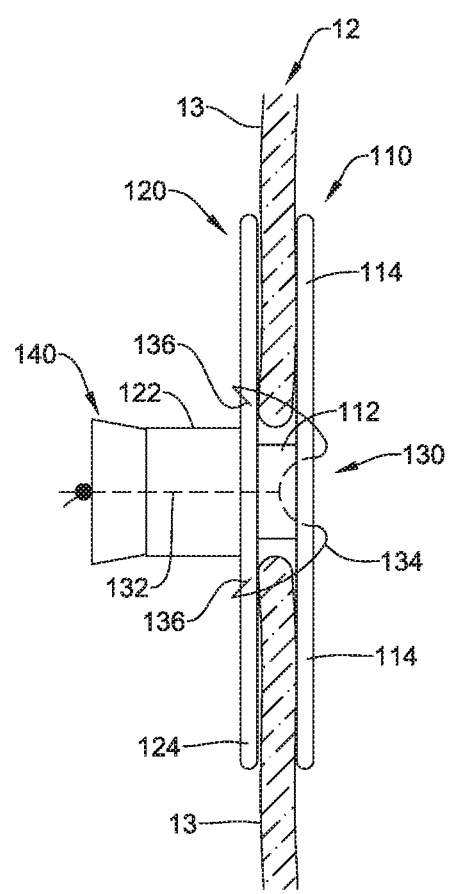

After deploying the securement element 140 adjacent the first axial core 112 and/or the second axial core 122, the securement element 140 may be advance distally into engagement with the first axial core 112 and/or the second axial core 122 as tension is applied to the central tensioning element 132. When tension is applied to the central tensioning element 132 in this way, the hook 136 at the free end of each of the plurality of arms 134 engages the mesh portion 124 of the second implant section 120 and/or the plurality of arms 134 may engage the first axial core 112 of the first implant section 110 such that the second implant section 120 and the first implant section 110 are urged towards each other. In some embodiments, the plurality of arms 134 may deflect and/or deform proximally within the first axial core 112 when the central tensioning element 132 is under tension, as seen in FIG. 12. Under these conditions, the plurality of arms 134 may act as a spring element to assist in maintaining tension on the central tensioning element 132.

After applying tension to the central tensioning element 132, the securement element 140 may be fixedly attached and/or secured to the central tensioning element 132 and/or fixedly attached and/or secured in place along the central tensioning element 132, for example by a knot, a crimp, adhesive(s), mechanical fastener(s), and/or other suitable fixation means, such that tension is maintained on the central tensioning element 132 and the plurality of arms 134. In some embodiments, the securement element 140 may be configured to engage the first axial core 112 and/or the second axial core 122 to maintain the central tensioning element 132 under tension, as seen in FIG. 12 for example. Other configurations of the securement element 140 are also contemplated. For example, in some embodiments, the securement element may extend over an outer surface of the second axial core 122 and/or abut a proximal end of the second axial core 122 (e.g., a cap, a flange, etc.).

Figure 13:
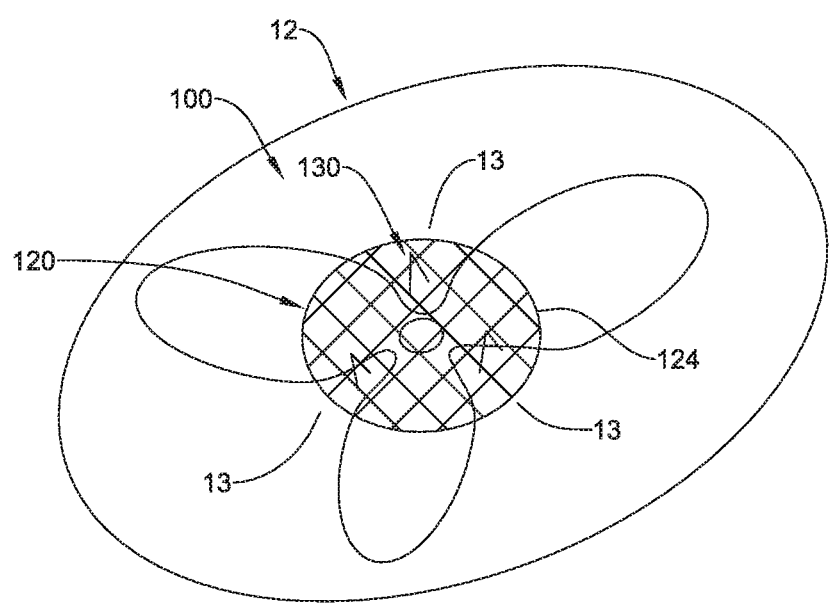
FIG. 13 illustrates the heart valve repair implant deployed in a tricuspid valve.
Figure 14:
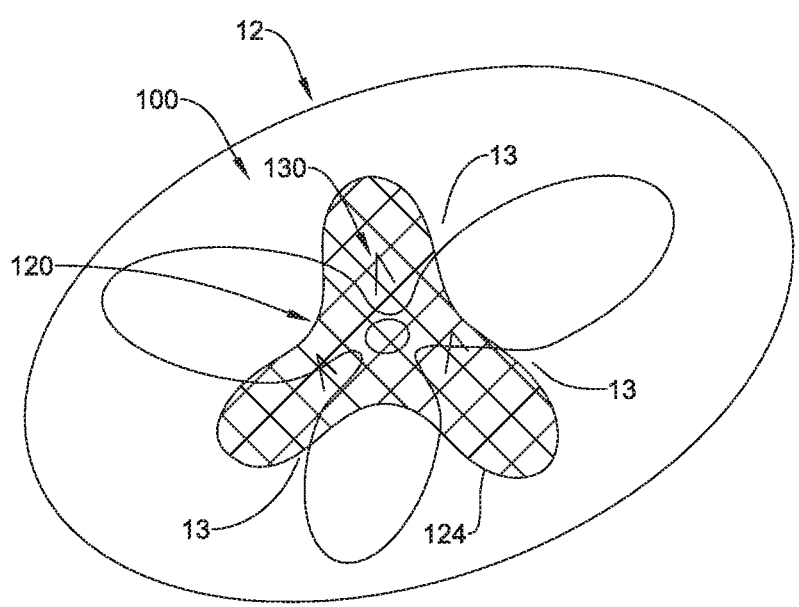
FIG. 14 illustrates an alternative configuration of the heart valve repair implant deployed in a tricuspid valve.

FIGS. 13 and 14 illustrate a partial perspective view of an example heart valve repair implant 100 disposed within a defective heart valve (e.g., the tricuspid valve 12, etc.), as seen from the upstream side of the plurality of valve leaflets 13. As noted above, the heart valve repair implant 100 may squeeze at least a portion of each valve leaflet 13 between the first implant section 110 (not shown) and the second implant section 120, and the third implant section 130 may extend axially through the first implant section 110 (not shown), the second implant section 120, and the plurality of valve leaflets 13. In at least some embodiments, the third implant section 130 and/or the plurality of arms 134 may assist in retention of the plurality of valve leaflets 13 between the first implant section 110 and the second implant section 120. For example, the third implant section 130 may prevent the plurality of valve leaflets 13 from slipping and/or translating relative to the first implant section 110 and the second implant section 120 during heart function (e.g., systole and/or diastole).

As seen in FIG. 13, in some embodiments, the mesh portion 124 of the second implant section 120 may define an outer perimeter or outer extent having a substantially circular shape in the expanded configuration. FIG. 14 illustrates an alternative configuration wherein the mesh portion 124 of the second implant section 120 may define an outer perimeter or outer extent having a multi-lobed shape in the expanded configuration. In some embodiments, the multi-lobed shape may include 2 lobes, 3 lobes, 4 lobes, 5 lobes, 6 lobes, or another suitable quantity of lobes. For the purpose of illustration only, the mesh portion 124 of the second implant section 120 is shown in FIG. 14 with the multi-lobed shape having 3 lobes. In some embodiments, the lobes may correspond to and/or align with the plurality of valve leaflets 13. As may be seen in FIGS. 13 and 14, after deployment and/or implantation of the heart valve repair implant 100, a plurality of openings through the defective heart valve (e.g., the tricuspid valve 12, etc.) may be formed to allow for blood passage through the heart valve (e.g., the tricuspid valve 12, etc.) during diastole. As illustrated in FIGS. 13 and 14, the plurality of arms 134 may extend through the plurality of valve leaflets 13. In some embodiments, at least some of the plurality of arms 134 may not extend through the plurality of valve leaflets 13 and/or may be positioned within the plurality of openings through the defective heart valve (e.g., the tricuspid valve 12, etc.) and/or between free edges of the plurality of valve leaflets 13 to engage the mesh portion 124 of the second implant section 120.

The materials that can be used for the various components of the heart valve repair implant 100, the first implant section 110, the second implant section 120, the third implant section 130, the securement element 140, the fourth elongate shaft 142, the delivery catheter 160, the first elongate shaft 170, the second elongate shaft 180, and/or the third elongate shaft 190, etc. (and/or other systems disclosed herein) and the various elements thereof disclosed herein may include those commonly associated with medical devices. For simplicity purposes, the following discussion makes reference to the heart valve repair implant 100, the first implant section 110, the second implant section 120, the third implant section 130, the securement element 140, the fourth elongate shaft 142, the delivery catheter 160, the first elongate shaft 170, the second elongate shaft 180, and/or the third elongate shaft 190, etc. However, this is not intended to limit the devices and methods described herein, as the discussion may be applied to other elements, members, components, or devices disclosed herein, such as, but not limited to, the heart valve repair implant 100, the first implant section 110, the second implant section 120, the third implant section 130, the securement element 140, the fourth elongate shaft 142, the delivery catheter 160, the first elongate shaft 170, the second elongate shaft 180, and/or the third elongate shaft 190, etc. and/or elements or components thereof.

In some embodiments, the heart valve repair implant 100, the first implant section 110, the second implant section 120, the third implant section 130, the securement element 140, the fourth elongate shaft 142, the delivery catheter 160, the first elongate shaft 170, the second elongate shaft 180, and/or the third elongate shaft 190, etc., and/or components thereof and/or associated therewith (such as, but not limited to, the first axial core 112, the plurality of spines 114, the second axial core 122, the mesh portion 124, the central tensioning element 132, the plurality of arms 134, etc.), may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum, platinum iridium alloys, platinum enriched stainless steel, and/or other platinum alloys; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the heart valve repair implant 100, the first implant section 110, the second implant section 120, the third implant section 130, the securement element 140, the fourth elongate shaft 142, the delivery catheter 160, the first elongate shaft 170, the second elongate shaft 180, and/or the third elongate shaft 190, etc., and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the heart valve repair implant 100, the first implant section 110, the second implant section 120, the third implant section 130, the securement element 140, the fourth elongate shaft 142, the delivery catheter 160, the first elongate shaft 170, the second elongate shaft 180, and/or the third elongate shaft 190, etc. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the heart valve repair implant 100, the first implant section 110, the second implant section 120, the third implant section 130, the securement element 140, the fourth elongate shaft 142, the delivery catheter 160, the first elongate shaft 170, the second elongate shaft 180, and/or the third elongate shaft 190, etc. to achieve the same result.

In some embodiments, a degree of Magnetic Resonance Imaging (MRI) compatibility is imparted into the heart valve repair implant 100, the first implant section 110, the second implant section 120, the third implant section 130, the securement element 140, the fourth elongate shaft 142, the delivery catheter 160, the first elongate shaft 170, the second elongate shaft 180, and/or the third elongate shaft 190, etc. For example, the heart valve repair implant 100, the first implant section 110, the second implant section 120, the third implant section 130, the securement element 140, the fourth elongate shaft 142, the delivery catheter 160, the first elongate shaft 170, the second elongate shaft 180, and/or the third elongate shaft 190, etc., and/or components or portions thereof, may be made of a material that does not substantially distort the image and create substantial artifacts (e.g., gaps in the image). Certain ferromagnetic materials, for example, may not be suitable because they may create artifacts in an MM image. The heart valve repair implant 100, the first implant section 110, the second implant section 120, the third implant section 130, the securement element 140, the fourth elongate shaft 142, the delivery catheter 160, the first elongate shaft 170, the second elongate shaft 180, and/or the third elongate shaft 190, etc., or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the heart valve repair implant 100, the first implant section 110, the second implant section 120, the third implant section 130, the securement element 140, the fourth elongate shaft 142, the delivery catheter 160, the first elongate shaft 170, the second elongate shaft 180, and/or the third elongate shaft 190, etc., and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the first implant section 110, the second implant section 120, the mesh portion 124, and/or other elements disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A heart valve repair implant, comprising:
    a first implant section comprising:
        a first axial core; and
        a plurality of spines extending radially outward from the first axial core in an expanded configuration;
    a second implant section comprising:
        a second axial core configured to slide over the first axial core; and
        a mesh portion configured to extend radially outward from the second axial core in an expanded configuration;
    a third implant section comprising:
        a central tensioning element extending through the first axial core; and
        a plurality of arms extending radially outward from the central tensioning element and configured to extend axially between the plurality of spines and through the mesh portion; and
    a securement element disposed on the central tensioning element.

2. The heart valve repair implant of claim 1, wherein the plurality of spines is circumferentially spaced apart from each other around the first axial core.

3. The heart valve repair implant of claim 1, wherein the plurality of spines extends radially outward perpendicular to the first axial core in the expanded configuration.

4. The heart valve repair implant of claim 1, wherein the mesh portion forms a flattened disc structure in the expanded configuration.

5. The heart valve repair implant of claim 1, wherein the mesh portion is biased towards the expanded configuration.

6. The heart valve repair implant of claim 5, wherein the mesh portion is self-biased towards the expanded configuration.

7. The heart valve repair implant of claim 1, wherein the plurality of arms each includes a hook at a free end of its respective arm, each hook having a tip extending toward the first implant section.

8. The heart valve repair implant of claim 7, wherein each hook is configured to engage the mesh portion when the central tensioning element is under tension.

9. The heart valve repair implant of claim 8, wherein the securement element is configured to engage the first axial core or the second axial core to maintain the central tensioning element under tension.

10. A heart valve repair system, comprising:
    a first elongate shaft having a first implant section releasably attached at a distal end of the first elongate shaft, the first implant section comprising:
        a first axial core; and
        a plurality of spines extending radially outward from the first axial core in an expanded configuration;
    a second elongate shaft slidably disposed over the first elongate shaft, the second elongate shaft having a second implant section releasably attached at a distal end of the second elongate shaft, the second implant section comprising:
        a second axial core configured to slide over the first axial core; and
        a mesh portion configured to extend radially outward from the second axial core in an expanded configuration; and
    a third elongate shaft slidably disposed within the first elongate shaft, the third elongate shaft having a third implant section disposed proximate a distal end of the third elongate shaft, the third implant section comprising:
        a central tensioning element extending through the first axial core; and
        a plurality of arms extending radially outward from the central tensioning element and configured to extend axially between the plurality of spines and through the mesh portion.

11. The heart valve repair system of claim 10, wherein the first elongate shaft is threadably attached to the first axial core.

12. The heart valve repair system of claim 10, wherein the second elongate shaft is threadably attached to the second axial core.

13. The heart valve repair system of claim 10, further comprising a delivery catheter having a lumen extending from a proximal end to a distal end, wherein the delivery catheter is sized and configured to percutaneously navigate to a defective heart valve for delivery of the first implant section, the second implant section, and the third implant section to the defective heart valve.

14. The heart valve repair system of claim 13, wherein the plurality of spines is disposed between the first elongate shaft and the delivery catheter in a collapsed delivery configuration.

15. The heart valve repair system of claim 13, wherein the mesh portion is disposed between the second elongate shaft and the delivery catheter in a collapsed delivery configuration.

16. A heart valve repair implant for improving function of defective heart valve having a plurality of valve leaflets, comprising:
- a first implant section comprising a plurality of spines extending radially outward from a first axial core in an expanded configuration;
- a second implant section comprising a mesh portion configured to extend radially outward from a second axial core in an expanded configuration, the second axial core being disposed around the first axial core; and
- a third implant section comprising a plurality of arms extending radially outward from a central tensioning element extending through the first axial core, the plurality of arms being configured to extend axially between the plurality of spines and through the mesh portion;

wherein the first implant section is configured to be positioned on a downstream side of the plurality of valve leaflets, the second implant section is configured to be positioned on an upstream side of the plurality of valve leaflets, and relative axial translation of the first implant section and the second implant section towards each other squeezes at least a portion of each valve leaflet between the first implant section and the second implant section.

17. The heart valve repair implant of claim 16, wherein the plurality of arms is configured to pierce and extend through the plurality of valve leaflets squeezed between the first implant section and the second implant section.

18. The heart valve repair implant of claim 16, wherein when tension is applied to the central tensioning element, free ends of the plurality of arms engage the second implant section and the plurality of arms engages the first axial core such that the second implant section and the first implant section are urged towards each other.

19. The heart valve repair implant of claim 16, wherein the mesh portion defines an outer perimeter having a substantially circular shape in the expanded configuration.

20. The heart valve repair implant of claim 16, wherein the mesh portion defines an outer perimeter having a multi-lobed shape in the expanded configuration.

* * * * *